United States Patent [19]

Carney et al.

[11] Patent Number: 5,025,032

[45] Date of Patent: Jun. 18, 1991

[54] PHENYL BUTYL NITRONE COMPOSITIONS AND METHODS FOR TREATMENT OF OXIDATIVE TISSUE DAMAGE

[75] Inventors: John M. Carney, Lexington, Ky.; Robert A. Floyd, Oklahoma City, Okla.

[73] Assignees: Oklahoma Medical Research Foundation, Oklahoma City, Okla.; University of Kentucky Research Foundation, Lexington, Ky.

[21] Appl. No.: 422,651

[22] Filed: Oct. 17, 1989

[51] Int. Cl.$^5$ .......................................... A61K 31/415
[52] U.S. Cl. ................................................. 514/400
[58] Field of Search ........................................ 514/400

[56] References Cited

U.S. PATENT DOCUMENTS

| 3,296,145 | 1/1967 | Findlam et al. | 252/106 |
|---|---|---|---|
| 3,849,934 | 11/1974 | Dorschner et al. | 47/57.6 |
| 4,153,722 | 5/1979 | Campbell et al. | 424/304 |
| 4,197,314 | 4/1980 | Campbell et al. | 424/304 |
| 4,214,003 | 7/1980 | Campbell et al. | 424/301 |
| 4,224,340 | 9/1980 | Campbell et al. | 424/304 |
| 4,870,002 | 9/1989 | Kiel | 435/2 |

FOREIGN PATENT DOCUMENTS

PCT/SE87/0-0629 7/1988 European Pat. Off. .

OTHER PUBLICATIONS

Petkova et al., *Agressologie* 28, 8, pp. 833–834 (1987).
Hearse et al., *J. Mol. Cell. Cardiol.* 20, 213–223 (1988).
Bolli et al., *J. Clin. Invest.* 82, pp. 476–485 (Aug. 1988).
Weglickl et al., *Oxy-Radicals in Molecular Biology and Pathology*, pp. 357–364, (Proceedings of an Upjohn-UCLA Symposium held at Park City, Utah, Jan. 24–30, 1988) Editor: Alan R. Liss, Inc., N.Y.
E. Masini et al., *Agents and Actions*, vol. 27, 1/2 pp. 154–157 (1989).
Novelli et al., *Free Radicals in Liver Injury*, pp. 225–228 (IRL Press, Oxford, England).
Novelli et al., *Oxygen Free Radicals in Shock*, Int. Workshop, Florence 1985, pp. 119–124 (Karger, Basel 1986).
Hearse et al., *Circulation Research*, vol. 60, No. 3, pp. 375–383 (Mar. 1987).
Yanev et al., *Oxygen Free Radicals in Shock*, Int. Workshop, Florence 1985, pp. 193–196 (Karger, Basel 1986).
Ilieva et al., *Neurosciences*, vol. 12, pp. 223–227.
Chiu et al., *Transplantation Proceedings*, vol. XIX, No. 1, pp. 1077–1079, (Feb. 1987).
Hall et al., *J. of Neurotrauma*, vol. 6, 3, pp. 169–176 (1989).
Edward D. Hall, *Critical Care Clinics*, vol. 5, No. 4, pp. 793–805 (Oct. 1989).
Hamburger et al., *Circulatory Shock*, 29, pp. 329–334 (1989).
McKechnie et al., *Circulatory Shock*, 19, pp. 429–439 (1986).
Joe M. McCord, *The New England J. of Med.*, vol. 312, No. 3, pp. 159–163 (Jan. 1985).
Chandler et al., *J. of Pharm. Methods*, 14, pp. 137–146 (1985).
Baethmann et al., *Critical Care Medicine*, vol. 16, No. 10, pp. 972–977 (Oct. 1988).
K. A. Hossman, *Critical Care Medicine*, vol. 16, No. 10, pp. 964–971 (Oct. 1988).
Lars Ernster, *Critical Care Medicine*, vol. 16, No. 10, pp. 947–953 (Oct. 1988).
B. K. Siesjo, *Critical Care Medicine*, vol. 16, No. 10, pp. 954–963 (Oct. 1988).

*Primary Examiner*—Stanley J. Friedman
*Attorney, Agent, or Firm*—Kilpatrick & Cody

[57] ABSTRACT

Compositions for treating tissue damage from ischemia contain PBN, or active derivatives thereof, which are active during ischemia in preventing ATP depletion of the cells which predisposes them to subsequent injury during reperfusion, and which are active during reperfusion as oxygen radical scavengers, in a suitable pharmaceutical carrier for systemic or local administration, especially to the CNS, spinal column and eyes. Based on animal studies, the dosage for treating damage due to stroke is in the range of 10 to 300 mg/kg. Similar dosages are useful in treating damage resulting from free radical generation during inflammation, either as a product of infection or exposure to inflammatory agents or abusive agents, including drugs and alcohol.

18 Claims, 5 Drawing Sheets

PHENYL BUTYL NITRONE COMPOSITIONS AND METHODS FOR TREATMENT OF OXIDATIVE TISSUE DAMAGE

BACKGROUND OF THE INVENTION

This is generally in the area of compositions and methods for use thereof for the treatment of oxidative tissue damage such as that resulting from ischemia or inflammation, wherein the active compounds are phenyl butylnitrone (PBN) or derivatives thereof.

Oxygenated tissue suffers damage, in many cases permanent damage, if it becomes ischemic and is then reperfused. Oxygen free radicals have been implicated in the injury. Brain appears to be uniquely susceptible to ischemia/reperfusion injury, and neurons are more susceptible than glial cells. Certain areas of the brain, for example, the hippocampus and spinal cord, are more susceptible than other regions of the brain. As a result, ischemia/reperfusion injury to brain may have a multiplicative effect simply because of the necessity for complete integrity of all regions in order to have proper functioning.

Several mechanisms may cause ischemic brain damage. For example, the mechanisms responsible for selective neuronal vulnerability may be different from those that cause glial swelling and extensive brain edema, and a third set of events may underlie such gross functional aberrations as seizures. Siesjo, *Critical Care Med.* 16, 954-963 (1988), has grouped the numerous observations into four possible mechanisms to explain the injury in brain. These include: (A) calcium mediated cell death, (B) excitotoxic damage (glutamate buildup), (C) free radical events and (D) acidosis. It is likely that all four basic mechanisms are either interrelated or contribute collectively to the injury observed.

It now seems likely that selective neuronal vulnerability is, at least to some extent, an excitotoxic lesion that is triggered by the release of glutamate and/or aspartate from depolarized nerve endings. At the membrane and molecular levels, calcium influx via NMDA-activated channels is probably crucial, although osmolytic damage to dendritic spines and dendrites could contribute. It has never been satisfactorily explained, however, how ischemia could cause delayed neuronal death.

The mechanisms that cause laminar necrosis, glial destruction, and infarction are more speculative. The inability of the cells to regulate their volume may be caused by a molecular defect where edema is a conspicuous feature. Cells that possess coupled antiporters for $Na+/H+$ and $Cl-/HCO_3$ exchange may regulate pHi at the expense of volume regulation, so that edema may be coupled to acidosis.

When ischemia is accompanied by a delayed acidosis-related damage, it seems likely that the lowering of pH causes changes in protein structure and function, which "mature" with time and ultimately cause gross membrane dysfunction. It is tempting to assume that the primary lesion is an iron-catalyzed free-radical damage to membrane components, enhanced by the drastic lowering of pHi and/or pHe.

Free radicals have been postulated to be mediators of reperfusion damage. The important production sites of such radicals as the superoxide ($O_2-$) and hydroxyl (OH) species are the mitochondrial respiratory chain and the sequences catalyzed by cyclooxygenase and lipoxygenase. However, radicals are also formed furing autoxidation of many compounds (e.g., catecholamines). Several ischemic events favor a spurt of free-radical formation, e.g., those causing oxidation of polyenoic free fatty acids, release and reuptake of catecholamines, and oxidation of hypoxanthine by xanthine oxidase. Although all these events occur during recirculation, when the $O_2$ supply is restored, they represent metabolic cascades triggered by agonist-receptor interactions, energy failure, and/or calcium influx during the insult. Although free radical formation is a likely cause of ischemic damage, it has been difficult to directly demonstrate that such formation occurs and/or that it is sufficiently pronounced to overwhelm the antioxidative defense of the tissue, Curran, et al., *Mol. Cell. Biol.* 5, 167-172 (1985). In recent years, however, evidence has been obtained that ischemia may cause conjugated dienes and malondialdehyde to accumulate in the tissue. Nonetheless, it remains to be conclusively shown that free-radical damage to unsaturated acyl chains in phospholipids, to protein, or to nucleic acids constitutes an important part of the ischemic necrosis. At present, the evidence is relatively strong for an involvement of free-radical mechanisms in vascular injury, but not for damage affecting nerve and glial cells.

Reviews by Hall and Braughler, *Free Radical Biol. Med.* 6, 303-313 (1989), Kontos, *Physiology of Oxygen Radicals*, ed. Taylor, Matalon and Ward, pp. 207-216 (Am. Physiol. Soc., Bethesda, MD 1986), and Ernster, *Critical Care Med.* 16, 947-953 (1988), document a significant amount of evidence implicating oxidative damage in head and spinal cord injury as well as in hemorrhagic stroke and ischemic stroke. Most research which strongly implicates the primary role of oxidative damage in ischemia/reperfusion injury in brain can be grouped into either of two types of studies: those which show protection by addition of agents preventing peroxidative events, or those designed to observe free radicals.

Although no drugs are currently approved for clinical use in treating tissue damage due to ischemia, several compounds have been proposed as potentially being effective. Mannitol, an osmotic agent and an oxygen scavenger, has been added to reperfusion media and may limit damage to organs for transplantation. Superoxide dismutase (SOD) has been suggested as a means for limiting in vivo oxidative damage. The most promising compounds that interfere with peroxidation generation are the lazaroids, modified prednisones, described by J. M. McCall, *Acta Anesthesia Belgica*, First Antwerp Int. Trauma Symp., which have been reported to be efficacious if given during or after ischemia. For example, Hall, et al, *Stroke* 19, 997-1002 (1988), demonstrated that the 21-aminosteroid (474006F), which is known to prevent peroxidation in brain homogenate, as described by Braughler, et al., *J. Biol. Chem.* 262, 10438-10440 (1987), protected gerbils against brain damage induced by three hours of unilateral carotid artery occlusion. White and Aust and co-workers, *Adv. Free Radical Biol. Med.* 1, 1-17 (1985), and Babbs, *Resuscitation* 13, 165-173 (1986), have demonstrated that iron chelators protect animals from ischemia/reperfusion injury.

With regard to direct demonstrations of oxidative events during ischemia/reperfusion injury in brain, there are pertinent observations using spin-trapping techniques, salicylate hydroxylation, protein oxidation, and nucleic acid oxidative damage. Spin-trapping has provided clear evidence implicating free radical production during ischemia/reperfusion injury. Imaizumi, et al, *Neurological Res.* 8, 214-220 (1986), showed that the spin-trap PBN when incubated with rat brain homogenate of animals which had experienced very low oxygen pressure for 5 min was able to trap an apparently lipid-type radical. Kirsch, et al, *Pediatric Res.* 21, 202A (1987), stated in a preliminary note that PBN had trapped free radicals in post ischemic brains from animals pretreated with the spin-trap. McCay's group have spin trapped free radicals in mouse brain, *Arch. Biochem. Biophys.* 244, 156-160 (1986), and shown that spin-trapped free radicals of PBN are present in blood leaving the heart of intact dogs recovering from a "stunned" myocardium, *J. Clin. Invest.* 82, 476-485 (1988). As described, the free radicals spin-trapped are apparently lipid-type free radicals and appear within 1 min after release of occlusion and reach peak intensity about 5 min after reperfusion starts. PBN enhanced recovery of the post ischemic function of the "stunned" heart.

In summary, while PBN has been used in a number of research studies, there has been no data to support the proposition that it could be useful in vivo, particularly with respect to treatment of tissue damage in the central nervous system. In vivo, the drug must be able to (1) cross the blood brain barrier and (2) act in a manner which reduces tissue damage during or following ischemia.

It is therefore an object of the present invention to provide composition and methods for use thereof which are useful in preventing or reversing ischemic damage in vivo., especially in the CNS, spinal cord and eyes.

It is a further object of the present invention to provide compositions and methods for use thereof which are useful in preventing or reversing free radical damage in vivo resulting from infection and inflammation.

It is another object of the present invention to provide compositions and methods for use which prevent energy depletion of cells during ischemia.

It is still another object of the present invention to provide compositions and methods for use which are useful in the treatment of a variety of disorders in addition to those resulting from ischemia, including progressive neuronal loss from disease or drug and alcohol abuse and disorders resulting from photooxidation and exposure to high pressure or enriched oxygen.

SUMMARY OF THE INVENTION

Compositions for treating tissue damage from ischemia contain PBN, or active derivatives thereof, having the following general formula, in a suitable pharmaceutical carrier for intravenous administration.

wherein:
X is phenyl or wherein R is H, and n is a whole integer from 1 to 5; or

Y is a tert-butyl group that can be hydroxylated or acetylated on one or more positions; phenyl; or wherein W is Z is a $C_1$ to $C_5$ straight or branched alkyl group.

Based on animal studies, the dosage for treating damage due to stroke is in the range of 10 to 300 mg/kg.

The compositions are administered prior to or during ischemia in an effective dosage to prevent or reverse predisposition of the cells to damage resulting from depletion of ATP (as demonstrated by in vivo NMR) and damage from free radical generation following reperfusion. The preferred method of administration is intravenously in humans for treatment of stroke. The preferred method of administration for treating inflammation is by directed delivery to the site of inflammation. Examples of diseases which can be treated include stroke, meningitis, progressive neuronal loss due to Parkinson's disease, senile dementia, and drug abuse, disorders arising from exposure to high pressure oxygen or enriched oxygen environments, and bleeding into nervous tissue as a result of trauma.

DETAILED DESCRIPTION OF THE INVENTION

Following ischemia there is a significant increase in free radical production (both oxygen and carbon centered radicals). The initial damage to brain cells is thought to result from the peroxidation products with subsequent damage from secondary (carbon-centered) radicals. Eventually the metabolic and synthetic pathways are damaged to such an extent that the cell dies. PBN and functionally equivalent spin trapping derivatives that pass through the blood brain barrier, prevent cell damage during and subsequent to ischemia by decreasing or preventing ATP depletion, and still exhibit spin trapping of oxygen radicals are of benefit by bonding to the carbon-centered-free radicals to prevent further damage by the modified enzyme or other constituent. As used herein, a free radical scavenger or spin trap reagent is a molecule that will form a stable complex with a free radical. A free radical carbon trap is a molecule in which the free radical is localized on a carbon atom or a nitrogen atom.

α-phenyl t-butyl nitrone (PBN), and derivatives thereof, in a pharmaceutical vehicle suitable for intravenous administration are useful in preventing or reversing CNS damage following ischemia or inflammation. As used herein, ischemia is defined as a blockage of blood flow that results in a lesion in the central nervous system (CNS), including the spinal column and eyes. PBN has a number of advantages in the treatment of ischemia induced damage, including being able to pass through the blood brain barrier and having no measurable effect on normal or uninjured cells. PBN is the preferred active compound at this time, although a number of derivatives are also useful, including hydroxy derivatives, especially 2-, 3- or 4-hydroxy PBN and mono-, di- and trihydroxy tert-butyl nitrone; esters, especially esters which release 2-, 3, or 4-hydroxyphenyl t-butyl nitrone such as the acetoxy derivative, 2-, 3-, or 4-carboxyphenyl t-butyl nitrone, such as the ethyl derivative, or phenyl hydroxybutyl nitrone, such as the acetoxy derivative; alkoxyl derivatives, especially alkoxyl derivatives which release 2-, or 4-hydroxyphenyl t-butyl nitrone, such as the methyl derivative; and acetamide derivatives, especially acetamide derivatives which release 2-, or 4 aminophenyl t-butyl nitrone, such as the acetyl derivative; diphenyl nitrone (PPN) and the analogous diphenyl nitrone derivatives. As used herein, "PBN" refers to both α-phenyl t-butyl nitrone and derivatives thereof, unless otherwise stated. The active agent in the compositions is N-tert-Butyl-α-phenylnitrone (PBN) or derivatives thereof that are spin trap reagents and which also act to prevent ATP depletion of cells.

The general formula for PBN and useful derivatives thereof is:

wherein:
X is phenyl or wherein R is H, and n is a whole integer from 1 to 5; or

Y is a tert-butyl group that can be hydroxylated or acetylated on one or more positions; phenyl; or -continued Z is a $C_1$ to $C_5$ straight or branched alkyl group.

The compositions can also contain other active agents, such as tissue plasminogen activator, streptokinase, or other clot dissolving compounds, other compounds which are oxygen radical scavengers such as mannitol or compounds which prevent peroxidase generation, such as the lazaroids.

Examples demonstrate the utility of the compositions in preventing brain damage and death in animals following blockage of blood flow through the carotid artery to the brain. Exemplary dosages of PBN ranged from 32 to 300 mg/kg of body weight in gerbils. The effective range of PBN in humans and other mammals is between approximately 10 and 300 mg/kg. The compositions can be effectively administered prior to, during or after ischemia, and prevent or decrease the extent of cellular damage.

The use of compounds which are spin-traps that are capable of scavenging oxygen radicals during reperfusion following ischemia, and which act to block ATP depletion of the cell (which predisposes the cell to injury following ischemia), represents a truly unique approach to the management of post-ischemic pathologic conditions, and following ischemia associated with surgical procedures (e.g., by-pass surgery and transplantation of organs). Since the trapping of endogenous free radicals is specific for only those cells that have been exposed to the conditions that result in the production of free radicals, the traps will have little or no effect on normal cells. The beneficial effects will occur only in injured cells. Moreover, because the beneficial effect does not require the presence of specific receptors or specific enzymes, the spin traps offer a significant improvement in the treatment of ischemia/induced cellular dysfunction and necrosis.

In addition, these compounds should be extremely useful for the prophylactic treatment of chronic or periodic cytotoxic conditions that involve free radicals. The CNS disease conditions that are expected to be treatable using such compounds include stroke, transient ischemic attacks, Alzheimer necrosis, continued cell loss in Parkinsonism, meningitis, cardiac resuscitation-induced brain damage, and damage arising as a result of trauma, especially head and spinal injuries with associated bleeding from surrounding tissues into the nervous tissues. It is expected that these compositions can also be used to treat a variety of other disorders including damage resulting from exposure to high pressure oxygen or oxygen - enriched environments, especially damage to the eyes resulting from placing very premature babies on high oxygen respirators, drug and/or alcohol abuse - induced damage to the CNS, as well as other organs, and damage resulting from exposure to ionizing radiation or photooxidation.

The PBN is preferably administered systemically, most preferably intravenously, or orally, since this is the most rapid and efficient means for directing the active compound to the site of free radical generation. However, other methods of administration can be used, as when PBN is administered intraperitoneally in the examples, or intranasally through the pulmonary tract. The PBN can alternatively be administered locally, by intramuscular or subcutaneous injection, ointment, or delayed release implant.

Preferred pharmaceutical carriers for intravenous administration are saline or phosphate buffered saline at physiological pH. In the preferred method, PBN is delivered to the patient intravenously in a dosage in the range of 10 mg/kg/hr, most preferably in the range of one to three mg/kg/hr. The dosage can be determined for the specific disease condition and/or species by conducting measurements, as described in detail below. In general, an effective dosage is that amount of PBN that reduces enzyme activity loss by 25%, decreases cell death by 25%, and/or maintains 25% or more of normal function.

The present invention will be further understood with reference to the following non-limiting examples demonstrating methods for determining effectiveness of PBN administration for treatment of injury arising from ischemia or inflammation and demonstration in animals of the prevention and/or reversal of damage from ischemia.

Gerbil Stroke Model

An accepted animal model for determining the effect of a compound on injury arising from a stroke is described by Chandler, et al., *J. Pharm. Methods* 14, 137-146 (1985). Briefly, Mongolian gerbils are anesthetized with pentobarbital (40 mg/kg). A ventral midline incision is made in the neck. Common carotids are exposed and separated from the vagosympathetic nerve trunk. A loop of unwaxed dental floss (Johnson and Johnson) is placed around each carotid. The ends of the floss are each passed through one of the lumens of a double lumen catheter (Dural Plastics and Engineering, Dural, NSW, Australia). The catheter and dental floss are passed through the dorsal musculature and exited at the dorsal surface of the neck. The catheter is fixed in position, directly above the carotid artery, using cyanoacrylate adhesive at the exit site. The dental floss length is marked in order to assure that the animal does not occlude the carotid during daily cleaning and exploratory activity. The ventral incision is closed with 9 mm wound clips. After 48 hrs following instrumentation, ischemia is produced by gently pulling the looped dental floss until the artery is occluded. Occlusion of the artery is associated with loss of consciousness, ptosis and a change in breathing pattern. Previous studies, using direct observation, have demonstrated that complete interruption of flow occurs under these conditions. The occlusion is maintained for 10 minutes and then the dental floss removed to allow complete reperfusion. After reperfusion, the catheter is trimmed flush with the surface of the neck.

The animals, male gerbils (50-60 gms), are purchased from Tumblebrook Farm, West Brookfield, Mass., and housed in groups of three for at least one week prior to instrumentation. Following surgery, the gerbils are singly housed in order to avoid the possible accidental induction of ischemia by cage mates. Food and water are available ad libitum in the home cage. All gerbils are maintained under a 12 hr light/dark cycle.

EXAMPLE 1

Determination of the Extent of Peroxidation Damage in Brain Tissue

Measurement of Tissue Damage by Free Radical Generation

Tissue damage can be measured as a function of the generation of free radicals, protein carbonyl concentration increase, and decrease in glutamine synthetase enzymatic activity.

Free radicals are found in ischemia/reperfusion injured gerbil brains. There are several methods effective for measuring the generation of free radicals, including spin trapping and salicylate hydroxylation. Salicylate hydroxylation can be used to monitor hydroxyl free radicals in vivo, since hydroxylation products (2,5-and 2,3-dihydroxybenzoic acids, DHBA) are present in the brains of gerbils pretreated with salicylate. The amount of DHBA correlates closely with the amount of brain injury observed in this model, as shown by Cao, et al., *Neuroscience Lett.* 88, 233–238 (1988). Oxidative damage to gerbil brain proteins can be assessed by protein carbonyl group increase, which occurs as the ischemic-lesioned gerbil brain is allowed to reperfuse. Overall tissue necrosis is also indicated by a decrease in the enzymatic activity of glutamine synthetase (GS) in ischemic-lesioned gerbil brain. This decrease increases as reperfusion time increases, such that at 60 min the GS activity is decreased about 35% from normal values. The enzymatic activity of GS is highly sensitive to metal catalyzed oxidative damage. Therefore its loss supports the notion that metal catalyzed oxidative damage does occur in the reperfusion phase of the ischemic-lesioned gerbil brain. GS enzymatically converts glutamate to glutamine and thus a decrease in its activity may allow the buildup of glutamate, an excitatory toxic amino acid.

Utilizing the ischemia/reperfusion lesioned brain of gerbils, it was demonstrated that oxidative damage was occurring, with the evidence as follows: (1) increased levels of salicylate hydroxylation products, implicating increased hydroxyl free radical flux in lesioned brain, (2) increased levels of protein oxidation and a loss of glutamine synthetase activity in lesioned brain, (3) free radical formed from spin-traps in lesioned brains, (4) spintrap mediated protection from brain ischemia/reperfusion injury, and (5) an increased peroxidation capacity of brain during the reperfusion phase after an ischemic insult.

Demonstration of in Vivo Oxygen Free Radical Flux by Spin-Trapping and HPLC with Electrochemical Detection Spin-trapping and HPLC with electrochemical detection (LCED) are used to quantitate hydroxylation products of salicylate, formed in part by hydroxyl free radical addition, and hydroxyl free radical adducts to DNA and RNA. The extreme sensitivity of the LCED methodology, on the order of $10^3$ to $10^4$ gain over optical methods, is a distinct advantage when attempting to ascertain the flux of oxygen free radicals in vivo, which may only reach $10^{-9}$ M under high oxidative stress conditions. It has been demonstrated in biochemical systems that OH radicals could be trapped by salicylate and quantitated using LCED.

Electron spin resonance of brain lipid extract is measured as follows. Gerbils are administered spin-trap dissolved in saline stored cold (protected from light) I.P. 1 hr prior to treatment. Gerbils are given an ischemia/reperfusion treatment, or in the case of sham-operated controls, placed in the animal holder but not occlusion, for a defined period. The gerbils are killed by decapitation. The brains are removed and placed on a cooled stage within 2 min. The cortex of brain is isolated cold and stored at $-80°$ C. for about one week until it is extracted. The cortex is homogenized at ice temperature in a 0.5% NaCl solution (5 gm/ml) and the homogenate is then extracted with 2:1 chloroform-methanol mixture (v/v) to a final dilution of 20-fold the volume of the tissue sample. The crude extract is washed thoroughly with 0.5% NaCl (5:1, v/v) and the mixture is allowed to separate into two phases by standing at 4° C. for 2 hr. The organic phase is recovered and bubbled with $N_2$ to obtain a concentration that is needed or the solvent of the organic phase is evaporated to dryness and the residue redissolved in chloroform. Finally, the samples are transferred to a Pasteur pipette (sealed at the capillary end) and bubbled with $N_2$ for 5 min. The pipettes are then placed in the sample cavity of an IBM Bruker ESP300 EPR spectrometer and scanned for the presence of spin adducts. The usual spectrometer settings are as follows: Microwave power 19.8 mW; modulation amplitude 0.975G, time constant 1310.72 ms; scan range 100 G; and scan time 6 min. All spectra are recorded at room temperature. The coupling constants can be directly obtained from the instrument and since since the instrument is controlled by an online computer, simulated spectra of a mixture of spin-trapped free radicals can be compared with the bona fide spectrum obtained in order to make prediction regarding the trapped free radicals. An extensive data base of spin coupling constants taken in different solvents using different systems is used for comparison purposes.

Spin-traps react with free radicals to form adducts, the electron spin resonance (ESR) spectrum, which provides a mechanism to deduce the chemical identity of the free radicals trapped. The method used for in vivo spin trapping was developed by Dr. P. B. McCay in combination with Dr. Ed Janzen, as reported by Lai, et al., *Arch. Biochem. Biophys.* 244, 156–160 (1986). Free radicals have been spin-trapped in ischemia/reperfusion injury in rat heart by Bolli and McCay, *J. Clin. Invest.* 82, 476–485 (1988).

The production of free radicals during ischemia/reperfusion induced injury in the gerbil brain was tested using spin trapping. Both treated and control animals were administered the spin trap PBN ($\alpha$-phenyl-t-butyl nitrone) before the experimental treatments. The data demonstrate that large free radical signals were obtained from the extracts of brains of ischemia/reperfusion treated gerbils in contrast to very little signals from sham-operated control animals. Surprisingly, the radicals are not what would be expected when a spin-trap reacts with a free radical to produce a spin adduct. A six-line spectrum is expected from the spin-adduct of a free radical of PBN. The six-line spectrum is due to the free electron interacting with the spin $\frac{1}{2}$ nuclear magnetic moment of the proton as well as the spin of 1 from the nitrogen of the nitroxyl group. In contrast, these spectra are only three lines, and are therefore due to the free electron interacting with the nitroxyl nitrogen only, which means that available protons are displaced at a distance such that they are not influencing the free electron.

The most likely explanation for the results is that PBN first traps a free radical, possibly a lipid carbon free radical, after which the spin-adduct is then oxidized to a nitrone which then traps another free radical, yielding a nitroxide having properties producing the observed spectra.

Two other spin-traps, DMPO (5,5-dimethylpyrroline-N-oxide) and POBN (α-pyridyl-1-oxide-N-t-butyl-nitrone), both of which have different chemical structures from PBN, yielded nitroxide spectra (very similar, 3-lines, yet with slightly different nitrogen coupling constants and different intensities) as with PBN in the ischemia/reperfusion treated gerbils. It is pertinent to note that if the chloroform/methanol extract of brains of animals which have been pretreated with PBN is allowed to stand at room temperature for 24 hours, then the 3-line signal decays. If, however, more PBN is then added to the extracts and it is then incubated for 24 hours, trapped radial signals are observed in the extract of ischemic/reperfusion animals, but signals are not seen in the sham-operated controls. Computer simulation of the signals developing show that three free radicals are present. One has parameters equivalent to the three line nitroxide observed previously and the other two are spin-trapped carbon free radicals, possibly lipid radicals. These observations indicate that oxidative events were started in the ischemic brains but not in the sham-operated controls and these events are carried over, at least in part, in the lipid extracts.

Demonstration of Ischemia/Reperfusion Induced Increased Peroxidation Capacity of the Brain Brain homogenate at ice temperature does not spontaneously peroxidase, yet if the temperature is raised to 37° C. there is, in contrast to almost all other tissue homogenates, spontaneous peroxidation. The rate of peroxidation varies with brain region and is highly correlated with the total iron content of the brain region. Gerbil brain homogenate peroxidizes more rapidly than rat brain. The susceptibility to peroxidation of brain homogenate after it has experienced an ischemia/reperfusion insult and the effect of time of reperfusion was determined. The data were collected from 176 gerbils. At every time point sham-operated animals were used as controls. The data show that after 10 min of ischemia there is, if reperfusion is not allowed to occur, a decrease in the rate of peroxidation. If reperfusion is allowed to occur after ischemia, then the rate of peroxidation increases significantly over sham-operated control animals in a time-course fashion. The increase is most rapid in the first 60 min then slows, reaching a maximum at 7 days following ischemia, after which it decreases to values which were still higher than controls at 14 days.

Brains from gerbils which have been pretreated with pentobarbital and then given a 15 min ischemia period followed by 15 min reperfusion have no increase in the amount of spontaneous peroxidation above sham-operated controls. Thus not only does pentobarbital protect gerbils from the damage brought about by ischemia/reperfusion injury, there is no increased peroxidation of the brain homogenate from pentobarbital treated animals as compared with untreated animals. Pre-treated animals lesioned by 15 min ischemia/15 min reperfusion had spontaneous brain homogenate peroxidation about 15% above sham-operated controls, demonstrating a direct correlation between increased brain homogenate peroxidation.

EXAMPLE 2

Figure 1:
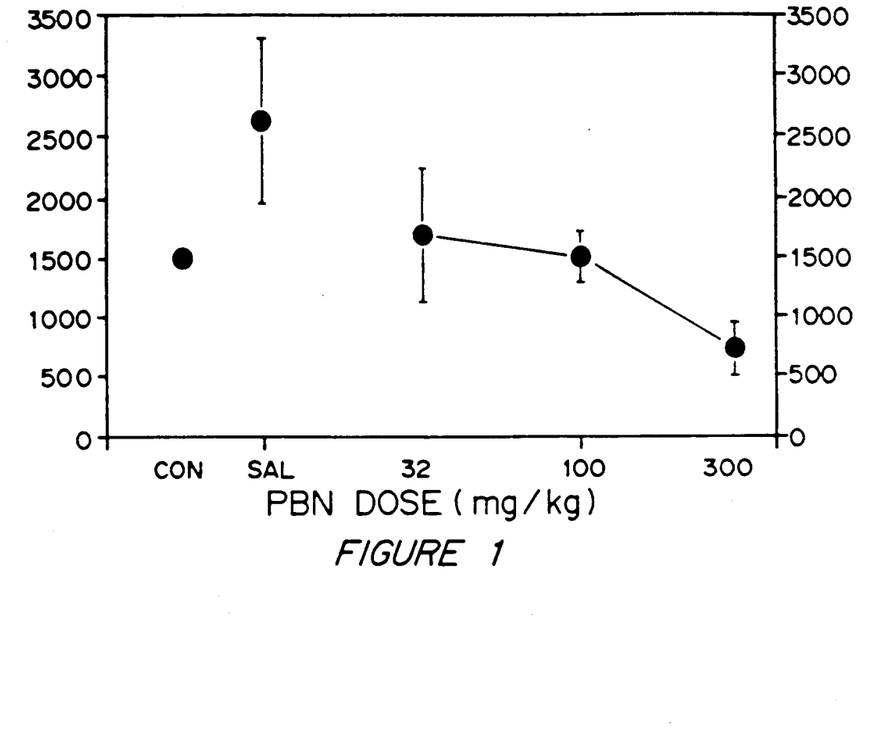
FIG. 1 is a graph of the dose-effect curve for the beneficial effects of PBN on transient ischemia-induced hyperactivity, plotting locomotor activity versus PBN dose in mg/kg. Young adult gerbils were given a single dose of PBN 1 hr. before 5 min of bilateral carotid occlusion. Twenty-four hours later the change in spontaneous locomotor activity was determined. Control (con) value represent the level of exploratory activity of a group of normal naive gerbils. Saline (Sal) values were determined in gerbils injected with saline 1 hr. prior to ischemia. Data presented represent the mean ($\pm$S.E.) for 6 gerbils per treatment group.

Demonstration of the Protective Effect of Spin-Traps in Ischemia/Reperfusion Induced Brain Injury in Gerbils The spin-trap PBN offers considerable protection to the gerbil from brain injury brought on by an ischemia/reperfusion insult and in addition helps prevent death which often accompanies the brain injury. The data demonstrating these statements are presented in FIGS. 1, 2, 3 and Table 1. Table 1 shows that animals given PBN I.P., dissolved in saline, at a dosage of 300 mg/kg, 60 min prior to 15 min ischemia, which is followed by 24 hr reperfusion, protected the animals from death, that is, the animals lived for longer than 7 days, the time point when lethality is evaluated. Of the control animals which received saline, 50% of the yound and 100% of the old gerbils had died as of the seventh day.

Figure 2:
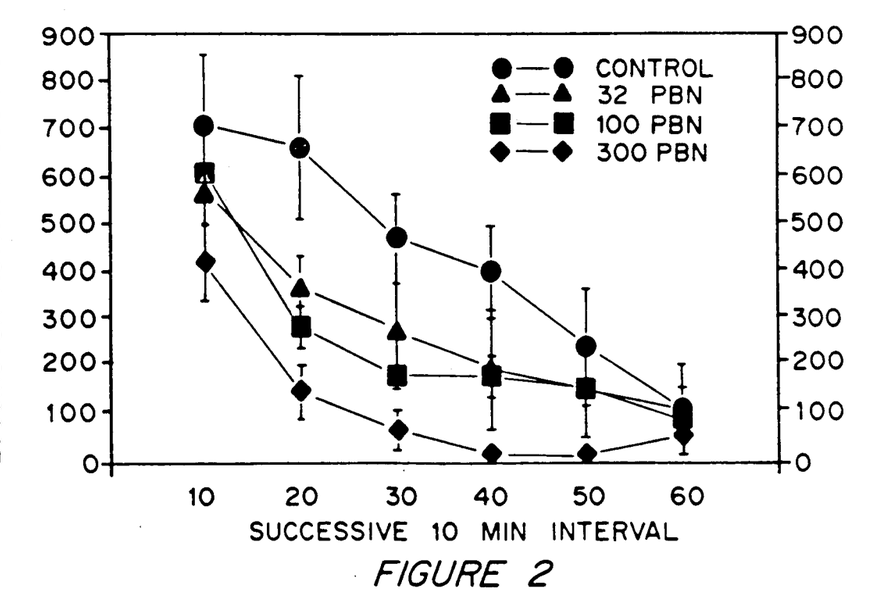
FIG. 2 is a graph of the effect of PBN on the levels of activity in successive 10 min intervals for the test described in FIG. 1. Data presented represents the means ($\pm$S.E.) for 6 gerbils per treatment group: control (-0-0-); 32 mg PBN/kg (-△-△-); 100 mg PBN/kg (-[]-[]-); and 300 mg PBN/kg (-◇-◇-).
Figure 3:
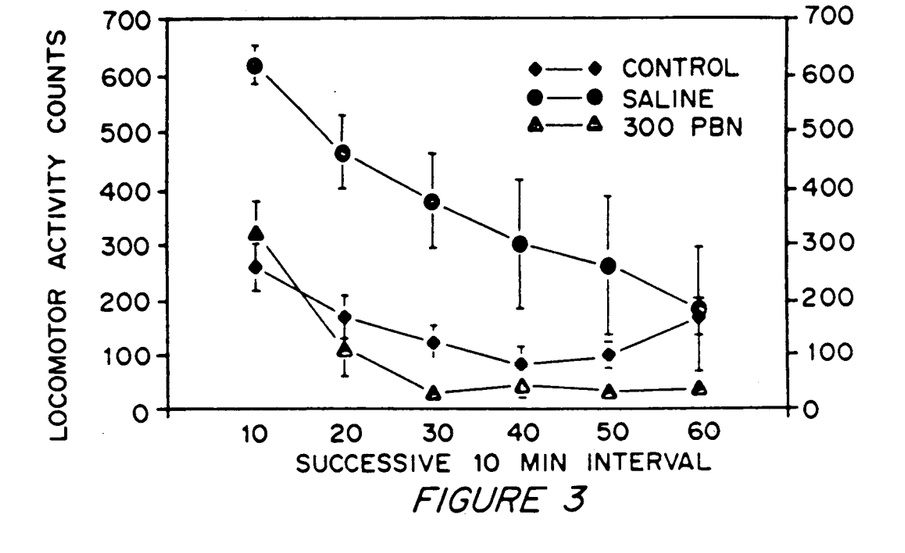
FIG. 3 is a graph of the effects of PBN on the post ischemic locomotor activity of aged gerbils (greater than 20 months of age) tested 24 hrs. after a 2 min period of ischemia, as described in FIG. 1. Control (-◇-◇-); saline (-0-0-); and 300 mg PBN/kg (-△-△-).
Figure 4:
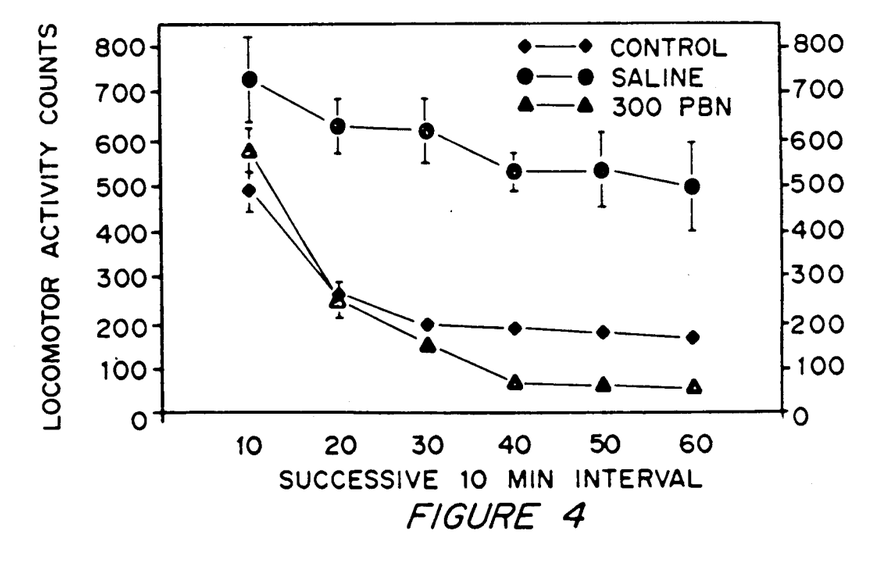
FIG. 4 is a graph of the effects of administration of 300 mg PBN on 15 min. ischemia-induced changes in spontaneous locomotor activity of gerbils, plotting locomotor activity counts versus time (minutes). Saline treated group (-0-0-) represents 5 of the 10 control gerbils (-◇-◇-) tested. The data for PBN (-△-△-) represents all 10 gerbils tested. Control values are for 6 gerbils. All data are expressed as the mean ($\pm$SE). Where no S.E. is indicated, it is within the dimensions of the symbol.

Gerbils, which have received a brain ischemic insult resulting in permanent injury, first exhibit a lethargic reaction then a characteristic increase in spontaneous locomotor activity above controls at 4 hours after ischemia. The lesion-induced hyperactivity continues for several days. Drugs that protect the animals from ischemia/reperfusion injury prevent the characteristic rise in spontaneous activity. PBN was effective at various dosages in protecting against ischemia/reperfusion induced hyperactivity, as demonstrated by Table 1 and FIG. 1. It can be seen that saline treated animals given a 5 min ischemia insult had hyperactivity significantly higher than sham-operated controls 24 hr after ischemia. However, animals which had received PBN at 32 or 100 mg/kg 1 hr prior to ischemia had no elevated hyperactivity. PBN at 300 mg/kg caused a decreased activity over controls. Data comparing activity at the 24 hr reperfusion time of sham-operated controls with 2 min ischemia, 5 min ischemia and 15 min ischemia lesioned animals, which had received either saline or 300 mg/kg PBN, are shown in FIGS. 2, 3 and 4. The data clearly demonstrate that the high dose of PBN caused a reduction in ischemia induced hyperactivity to levels of the control or lower.

TABLE 1

| Histopathological Scores in Gerbils 7 days after 5 min of Global Cortical Ischemia. | |
|---|---|
| Group | Score |
| Control (no ischemia) | 4.3 ($\pm$.5) |
| 32 mg PBN/kg | 2.5 ($\pm$.7) |
| 100 mg PBN/kg | 2.8 ($\pm$.4) |
| 300 mg PBN/kg | 1.7 ($\pm$.5) |

*N = 6 gerbils per group.

Figure 5:
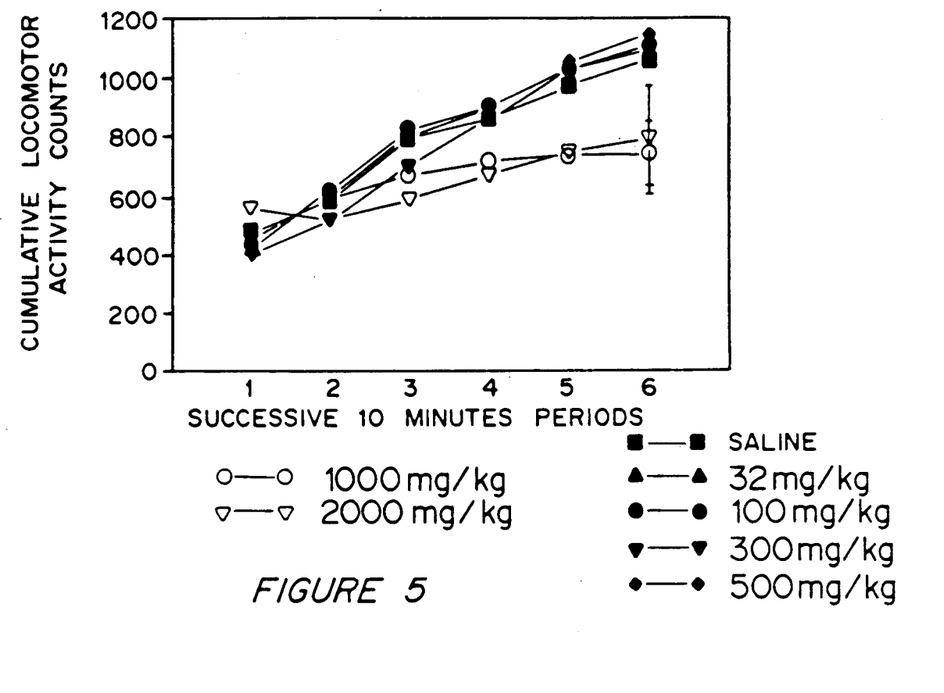
FIG. 5 is a graph comparing cumulative locomotor activity counts over successive 10 minute periods for non-ischemic animals receiving saline (dark []); 32 mg PBN/kg (dark △); 100 mg PBN/kg (.); 300 mg PBN/kg (dark inverted △); 500 PBN/kg (dark ◇); 1000 mg PBN/kg (0); and 2000 mg PBN/kg (inverted △).

In order to obtain parameters relative to acute toxicity of PBN, total cumulative activity of normal gerbils were investigated at a wide range of concentrations. The data are shown in FIG. 5. Only at PBN concentrations of 1000 mg/kg and higher was there any alteration in activity noted. PBN at 2000 mg/kg was not lethal to animals. The one noted effect at high PBN concentrations is an induced lethargic response which disappears after 24 hours.

Figure 6:
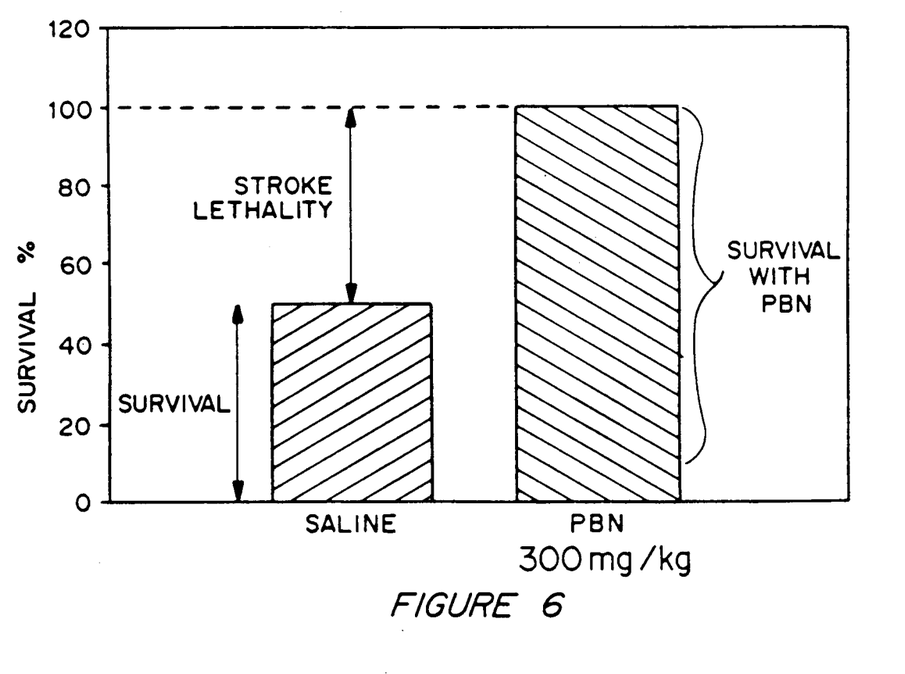
FIG. 6 is a bar graph comparing percent survival after a lethal occlusion of the carotid arteries in gerbils treated with either saline or 300 mg PBN/kg.

The effect of PBN administration on percent survival of animals given lethal strokes (15 min ischemia) is shown in FIG. 6. 50% of the animals given 15 minutes ischemia died. With pre-ischemic treatment with PBN, 100% of the animals survived.

Ischemia/reperfusion induced oxidative damage to brain proteins. Gerbil brains which had received various treatments were analyzed for carbonyl groups on proteins, a measure of oxidative damage to protein, and glutamine synthetase activity. The results are shown in FIGS. 7 and 8 and compared in FIG. 9.

Figure 7:
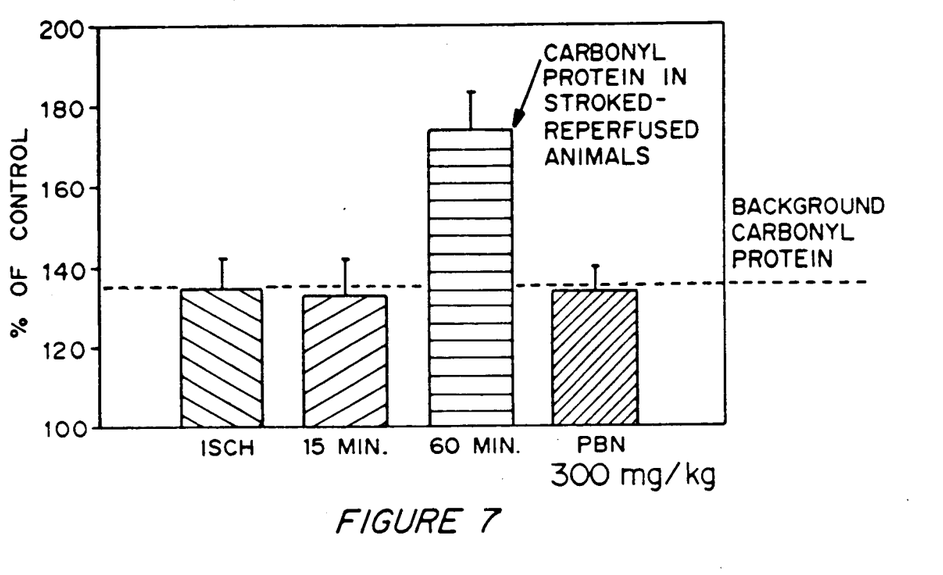
FIG. 7 is a graph comparing the percent carbonyl protein of control in gerbils that have been subjected to ischemia, ischemia followed by 15 minutes reperfusion, ischemia followed by 60 minutes reperfusion, and ischemia followed by 60 minutes reperfusion with pre-ischemia administration of 300 mg PBN/kg.

FIG. 7 shows oxidative damage to protein as measured by carbonyl content as a percentage of a control gerbil brain given a ten minute ischemia at the indicated time of reperfusion. 300 mg PBN/kg was administered one hour prior to the onset of ischemia. Carbonyl protein content was elevated above control levels in 10 min ischemia treated brains without reperfusion.

Reperfusion for 15 min did not enhance carbonyl protein above the ischemia only values. After 60 min reperfusion there was a significant increase in carbonyl protein. PBN pretreatment prevented this rise.

Figure 8:
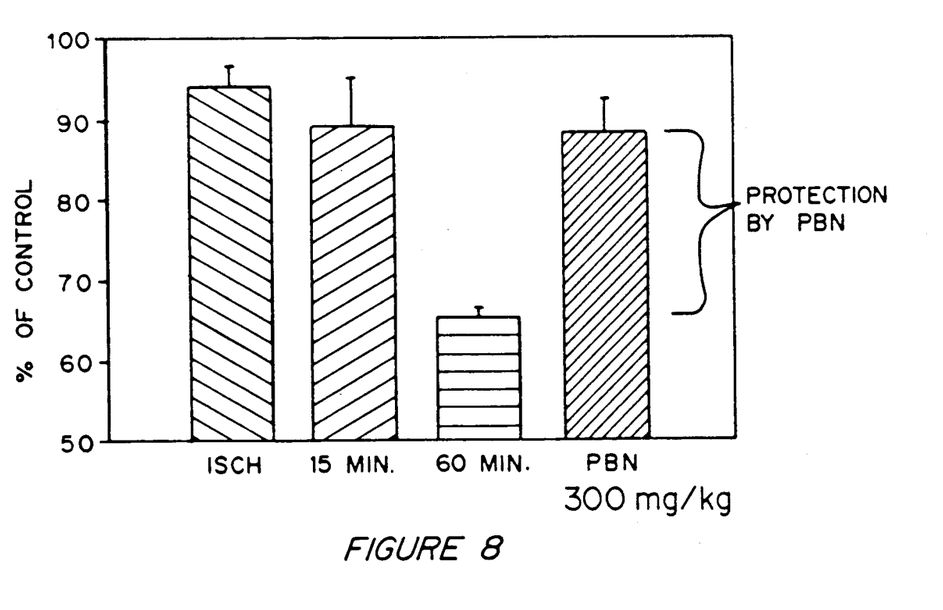
FIG. 8 is a graph comparing percent of glutamine synthase activity of control gerbils that have been subjected to ischemia, ischemia followed by 15 minutes reperfusion, ischemia followed by 60 minutes reperfusion, and ischemia followed by 60 minutes reperfusion with pre-ischemia administration of 300 mg PBN/kg.

FIG. 8 shows the oxidative damage to glutamine synthetase activity as a percentage of a control gerbil brain given a ten minute ischemia at the indicated time of reperfusion. 300 mg PBN/kg was administered one hour prior to the onset of ischemia. Glutamine synthetase (GS) activity was slightly lower than control values after ischemia with no reperfusion. With increasing reperfusion time, there was a dramatic loss in GS activity such that after 60 min reperfusion, only 65% of the activity remained. PBN pretreatment of the animals prevented this loss in GS activity. Since this enzyme is considered to be a glial cell marker, this data indicates post ischemic damage also occurs in glial cells.

Figure 9:
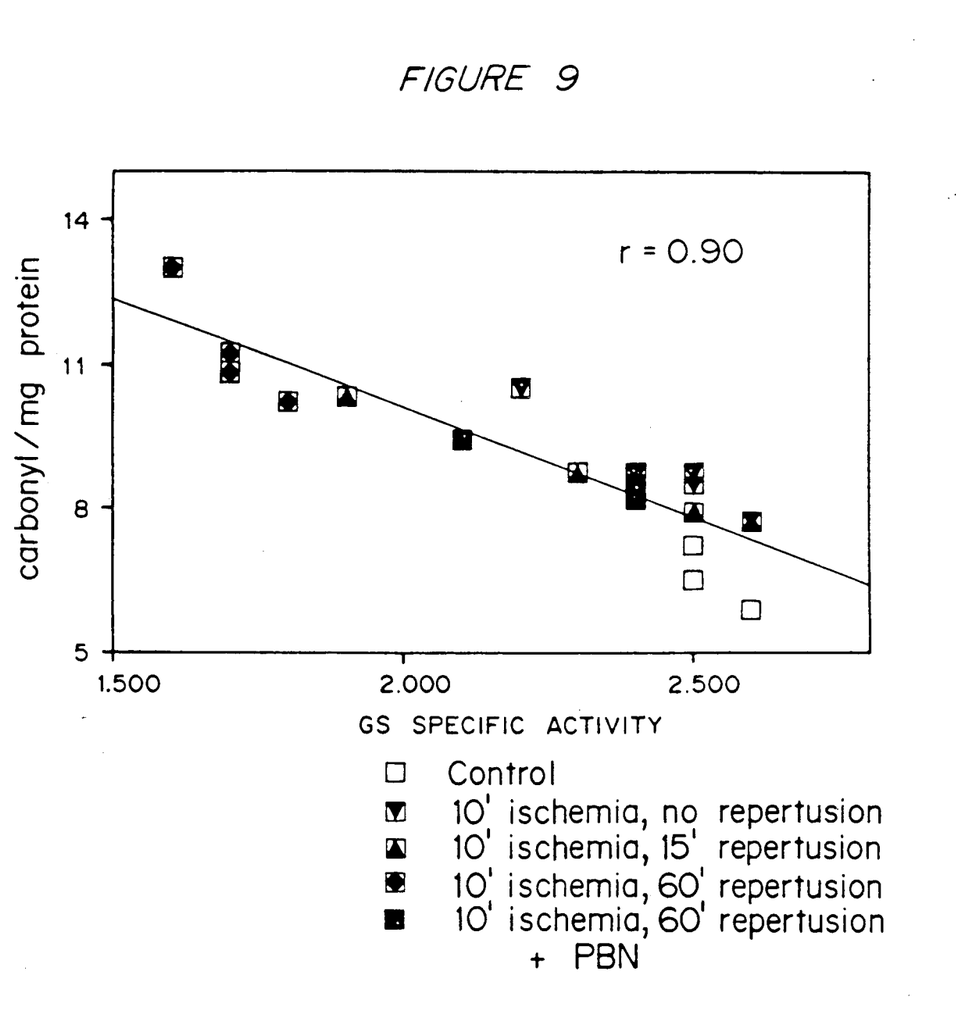
FIG. 9 is a graph correlating carbonyl/mg protein versus glutamine synthetase specific activity, control (-[]-[]-); 10 minutes ischemia, no reperfusion (-[inverted △]-[inverted △]-), 10 minutes ischemia, 15 minutes reperfusion ([△]-[△]-), 10 minutes ischemia, 60 minutes reperfusion (-[◇]-[◇]-), and 10 minutes ischemia, 60 minutes reperfusion and PBN (dark []).

FIG. 9 shows that there was a good correlation between the loss of GS activity versus accumulation of carbonyl protein when all of the samples analyzed are compared.

Ischemia/Reperfusion Induced Gene Expression

The levels of mRNA for c-fos and c-jun were examined in gerbil brain cortex after ischemia/reperfusion. The results of 10 min of ischemia followed by 60 min of reperfusion demonstrated that both c-fos and c-jun mRNA levels are elevated within 60 min after the insult. Control animals and animals subjected to the surgery showed lower levels of c-fos mRNA was markedly enhanced. Pentobarbital pretreatment, which protects the animals from ischemia/reperfusion injury, prevented the induced expression of the c-fos gene, whereas no pretreatment caused a large increase in c-fos mRNA. PBN pretreatment suppresses the level of c-fos induction in the ischemia/reperfusion injury.

Old gerbils are much more sensitive to brain ischemia/reperfusion injury than young animals, as shown in Table 2. Data are expressed as number surviving/total tested.

TABLE 2

Effects of PBN pretreatments on post reperfusion lethality in young adult gerbils (3-4 months of age).

| Treatment | Age | (300 mg PBN/kg) | Saline |
|---|---|---|---|
| control | young | 15/15 | 15/15 |
| 15 min ischemia | young | 10/10 | 5/10* |
| 10 min ischemia | retired breeders; (18 mo.) | 4/4 | 0/4 |

*All surviving gerbils were subsequently tested for behavioral effects at 24 hr. post-ischemia.

EXAMPLE 3

Effectiveness of Spin-Trapping Reagents Other Than PBN

In preliminary studies, the effectiveness of two other spintraps, DMPO and POBN, in preventing the acute effects of an ischemic insult to brain was tested. The results indicate that both DMPO and POBN appear to offer some protection, but DMPO was less effective than POBN which was less effective than PBN.

Modifications and variations of the present invention, compositions containing PBN and derivatives thereof, and methods using the compositions for the treatment of tissue damage resulting from ischemia or inflammation, will be obvious to those skilled in the art from the foregoing detailed description. Such modifications and variations are intended to come within the scope of the following claims.

We claim:

1. A method for in vivo treatment of oxidative CNS tissue damage resulting from ischemia or inflammation comprising:
   providing α-phenyl t-butyl nitrone and derivatives thereof having spin trapping activity and preventing ATP depletion in vivo in tissue and
   a pharmaceutically acceptable carrier for delivery of the α-phenyl t-butyl nitrone to the CNS of a patient.

2. The method of claim 1 wherein the phenyl butyl nitrone derivatives are selected from the group consisting of hydroxy PBNs, PBN esters, acetoxy PBNs, alkyl PBNs, alkoxyl PBNs, phenyl PBNs.

3. The method of claim 1 wherein the PBN derivative is functionalized to release in vivo a compound selected from the group consisting of 2-, 3-, and 4-hydroxyphenyl t-butyl nitrone; 2-, 3-, and 4-hydroxyphenyl t-butyl nitrone; 2-, 3-, and 4-carboxyphenyl t-butyl nitrone; and 2-, 3-, and 4-aminophenyl t-butyl nitrone.

4. The method of claim 1 comprising as the active ingredient α-phenyl t-butyl nitrone.

5. The method of claim 1 further comprising administering an agent selected from the group consisting of streptokinase, tissue plasminogen activator, mannitol, and lazaroids.

6. The method of claim 1 wherein the PBN and derivatives thereof is in a pharmaceutical carrier delivering an effective dosage to a patient to prevent reperfusion injury of CNS tissue.

7. The method of claim 1 wherein the PBN and derivatives thereof is in a pharmaceutical carrier delivering an effective dosage to a patient to prevent CNS tissue damage from inflammation.

8. The method of claim 1 wherein the PBN and derivatives thereof is provided in a dosage of 10 to 300 mg PBN/kg body weight.

9. The method of claim 1 wherein the composition is administered during or immediately after a stroke.

10. The method of claim 1 wherein the composition is administered to a patient having a progressive neuronal disorder.

11. The method of claim 1 wherein the composition is administered to a patient exposed to high pressure oxygen or an oxygen enriched environment.

12. The method of claim 1 wherein the composition is administered to a patient to mitigate damage to cells from exposure to a chemical agent.

13. The method of claim 1 wherein the composition is administered to a patient suffering from meningitis.

14. A composition for in vivo treatment of tissue damage resulting from ischemia or inflammation not associated with bacterial toxins comprising:

α-phenyl t-butyl nitrone and derivatives thereof having spin trapping activity and preventing ATP depletion in vivo in tissue of the formula:

wherein:

X is phenyl or wherein R is H, and n is a whole integer from 1 to 5; or

Y is a tert-butyl group that can be hydroxylated or acetylated on one or more positions; phenyl; or wherein W is C—CH₃, NH—C—Z, $$\overset{O}{\underset{\|}{C}}—CH_3, \overset{O}{\underset{\|}{C}}—OZ, \text{ or } Z; \text{ and}$$

Z is a $C_1$ to $C_5$ straight or branched alkyl group further comprising a compound selected from the group consisting of streptokinase, tissue plasminogen activator, mannitol and lazaroides a pharmaceutically acceptable carrier for intravenous administration to a patient, wherein the α-phenyl nitrone is in an amount effective to prevent tissue damage resulting from ischemia or inflammation not associated with bacterial toxins wherein the nitrone and further compound are present in effective amounts.

15. The composition of claim 14 wherein the phenyl butyl nitrone derivatives are selected from the group consisting of hydroxy PBNs, PBN esters, acetoxy PBNs, alkyl PBNs, alkoxyl PBNs, phenyl PBNs.

16. The composition of claim 1 wherein the PBN derivative is functionalized to release in vivo a compound selected from the group consisting of 2-, 3-, and 4-hydroxyphenyl t-butyl nitrone; 2-, 3, and 4-hydroxyphenyl t-butyl nitrone; 2-, 3-, 3-, and 4-carboxyphenyl t-butyl nitrone; and 2-, 3-, and 4-aminophenyl t-butyl nitrone.

17. The composition of claim 14 comprising as the active ingredient α-phenyl t-butyl nitrone.

18. The composition of claim 14 wherein the PBN and derivatives thereof is in a pharmaceutical carrier delivering an effective dosage to a patient to prevent reperfusion injury.

* * * * *